US012810961B2

(12) United States Patent
Edebratt et al.

(10) Patent No.: US 12,810,961 B2
(45) Date of Patent: Nov. 24, 2026

(54) METHOD OF QUALIFYING A SUBGROUP OF TARGET BINDING BIOMOLECULES FROM A LARGER GROUP OF TARGET BINDING BIOMOLECULES FOR ANALYSIS

(71) Applicant: Cytiva Sweden AB, Uppsala (SE)

(72) Inventors: Fredrik Edebratt, Uppsala (SE); Olof Karlsson, Uppsala (SE); Anna Lager, Uppsala (SE); Jens Larsson, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 1236 days.

(21) Appl. No.: 17/636,288

(22) PCT Filed: Sep. 8, 2020

(86) PCT No.: PCT/EP2020/075109

§ 371 (c)(1),
(2) Date: Feb. 17, 2022

(87) PCT Pub. No.: WO2021/052822

PCT Pub. Date: Mar. 25, 2021

(65) Prior Publication Data

US 2022/0336041 A1 Oct. 20, 2022

(30) Foreign Application Priority Data

Sep. 16, 2019 (GB) ..................................... 1913351

(51) Int. Cl.
*G16B 45/00* (2019.01)
*G01N 33/68* (2006.01)
*G16B 15/00* (2019.01)
*G16B 40/20* (2019.01)

(52) U.S. Cl.
CPC ......... *G16B 15/00* (2019.02); *G01N 33/6845* (2013.01); *G16B 40/20* (2019.02); *G16B 45/00* (2019.02)

(58) Field of Classification Search
None
See application file for complete search history.

(56) References Cited

U.S. PATENT DOCUMENTS

| | | | | |
|---|---|---|---|---|
| 2011/0212106 | A1* | 9/2011 | Lanzavecchia | ......... A61P 37/04 435/320.1 |
| 2015/0269312 | A1 | 9/2015 | Miles et al. | |
| 2019/0018923 | A1 | 1/2019 | Meshkin | |
| 2019/0194646 | A1 | 6/2019 | Faynboym | |

FOREIGN PATENT DOCUMENTS

| | | | |
|---|---|---|---|
| CN | 107067427 | A | 8/2017 |
| WO | 2013128031 | A1 | 9/2013 |
| WO | 2017197347 | A1 | 11/2017 |

OTHER PUBLICATIONS

PCT International Search Report and Written Opinion for PCT/EP2020/075109; mailed, Dec. 4, 2020 (12 pages).
Great Britain Search Report for GB Application No. 1913351.1; mailed, Feb. 21, 2020 (4 pages).
Abdiche et al. "High-throughput epitope binning assays on label-free array-based biosensors can yield exquisite epitope discrimination that facilitates the selection of monoclonal antibodies with functional activity," PLOS-ONE, vol. 9, No. 3, Mar. 1, 2014, p. e92491.
Chan, B.M. et al. "Flow Cytometry-Based Epitope Binning Using Competitive Binding Profiles for the Characterization of Monoclonal Antibodies against Cellular and Soluble Protein Targets", SLAS Discovery, vol. 23, 2018, pp. 613-623.
Brooks, B.D. et al. "High-throughput epitope binning of therapeutic monoclonal antibodies: why you need to bin the fridge", Curr. Drug Discover. Technol., vol. 11, 2014, pp. 109-112.
Chinese Office Action for corresponding application CN 202080064873.2; mailed May 31, 2024 (25 pages).
Japanese Office Action for corresponding application JP 2022-516713; mailed Jun. 3, 2024 (4 pages).

* cited by examiner

*Primary Examiner* — Christopher M Gross
(74) *Attorney, Agent, or Firm* — Eversheds-Sutherland (US) LLP

(57) ABSTRACT

Disclosed is a method of qualifying a subgroup of target binding biomolecules from a larger group of target binding biomolecules for analysis. A competitive immunoassay including a target protein is used to identify 100 interactions between different pairs of the target binding biomolecules and interaction profiles are generated 200. Each target binding biomolecule is allocated 300 to a bin representing an epitope family and identified bins are associated in a circular or semi-circular bin chart on a display with identified respective target binding biomolecule(s). Based on the association 400 between identified bins and identified respective target binding molecule(s) in the bin chart, a subgroup of target binding biomolecules is selected 500 for further analysis by selecting one or more of the target binding biomolecule(s) of one or more of the bins.

14 Claims, 8 Drawing Sheets

METHOD OF QUALIFYING A SUBGROUP OF TARGET BINDING BIOMOLECULES FROM A LARGER GROUP OF TARGET BINDING BIOMOLECULES FOR ANALYSIS

CROSS REFERENCE TO RELATED APPLICATIONS

This application claims the priority benefit of PCT/EP2020/075109, filed on Sep. 8, 2020, which claims the priority benefit to GB Application No. 1913351.1, filed on Sep. 16, 2019, the entire contents of which are incorporated herein by reference.

TECHNICAL FIELD

The present document relates to a method and system of qualifying a subgroup of target binding biomolecules from a larger group of target binding biomolecules for analysis.

BACKGROUND ART

Epitope binning may be used in the discovery and development of new therapeutics, vaccines, and in diagnostics. Epitope binning is a competitive immunoassay used to characterize and then sort a library of for example monoclonal antibodies against a target protein. Antibodies against a similar target may be tested against all other antibodies in the library in a pairwise fashion to see which antibodies block one another's binding to an antigen. Each antibody has a competitive blocking profile created against all of the other antibodies in the library. Epitope binning defines topological epitopes on a target protein in terms of the ability of the pairs of antibodies to bind simultaneously to the same target protein. If two different antibodies can bind at the same time, they bind to topologically distinct epitopes at the target protein. If they interfere with each other's binding, they bind to the same or overlapping epitopes. Closely related binning profiles indicate that the antibodies have the same or a closely related epitope and are "binned" together.

Epitope binning as such does not answer the question to what specific epitope of a target protein, antigen molecule, a certain antibody binds (i.e. epitope mapping), but groups a range of antibodies into different bins depending on their binding to different epitopes. If a specific epitope is known for some of the antibodies in an experiment the other antibodies grouped in the same bin could also bind to that specific epitope. As a result, the border line between epitope binning and epitope mapping is vague.

Epitope binning potentially may be a critical, early-stage, screening technique in a biologic drug discovery workflow. Engineering monoclonal antibodies (mAb) which target a specific functioning epitope on a target antigen usually is more important than finding high-affinity, tight-binding mAb, primarily because affinity maturation is a mature and cost effective protein engineering technique. With epitope binning, the top antibodies from each bin may be tested, allowing the therapeutically relevant epitopes to be identified more quickly and cost efficiently. Using epitope binning could decrease late stage failures. Using epitope binning the number of antibody candidates may be increased without increases in costs or cycle time; thus, epitope binning increases the overall probability of success. When affinity or other criterion is used as the primary selection tool, one can bias the results to a small number of epitopes. This limits the probability that functional epitopes are represented in the selected panel, or that candidates with otherwise desirable properties whose affinity could be matured are missed. When all candidates are grouped according to epitope first, i.e. binning, epitope diversity is maintained and the best performing antibodies in each bin can then be selected.

Binning experimental data may be displayed to a user in a so-called heat map, a table where the binding response levels (or other parameters) are displayed for all analysed pairs of antibodies and different colours/patterns are used to distinguish antibodies that compete for the same epitope and those that do not. The heat map may comprise a grid of squares (coloured or patterned), which represent interactions between antibodies. Squares of a first colour/pattern represent a blocking interaction between two antibodies, and squares of a second colour/pattern represent that that they can simultaneously bind to the antigen in different locations. A third colour/pattern may be used to represent ambiguous interactions. Other colours/patterns may be used to represent for example "one-direction" interactions, in which blocking occurs when one antibody is attached to the antigen first.

In US20150269312A1 is shown an alternative way to heat maps for sorting and displaying data from binning experiments. In this document node plots are shown, wherein nodes can be grouped together representing antibodies in a common bin. Nodes can be grouped together for antibodies that have the same blocking behaviour in both the ligand and analyte direction. Nodes can be grouped together by proximity between the nodes, such as clustering the nodes for a single bin close together. Nodes in a single bin can be represented by displaying an envelope, or outline, surrounding the nodes. Nodes can also be grouped by formatting the nodes themselves, such as by matching node colour/shape/border etc. Upon viewing the node plots it is possible for a viewer to determine which antibodies belong to which bin. The node plot can also comprise connections, e.g. lines, cords etc., between the nodes, representing interactions between antibodies.

Both heat maps and node charts may, however, be difficult, especially for inexperienced users, to quickly understand and to interpret the association of the binning experimental data. Hence, there is need for improved binning methods and systems, which offer simpler interpretation and extraction of associations of binning experimental data.

SUMMARY OF THE INVENTION

It is an object of the present disclosure to provide an improved binning method and system, which offer simpler interpretation and extraction of associations of binning experimental data.

The invention is defined by the appended independent patent claims. Non-limiting embodiments emerge from the dependent patent claims, the appended drawings and the following description.

According to a first aspect there is provided a method of qualifying a subgroup of target binding biomolecules from a larger group of target binding biomolecules for analysis. The method comprising, in a competitive immunoassay including a target protein, identifying interactions between different pairs of the target binding biomolecules. Using a processing unit, generating interaction profiles for said target binding biomolecules from said identified interactions. Using a binning unit, allocating each target binding biomolecule to a bin, wherein each bin represents an epitope family and target binding biomolecules sharing a common interaction profile are allocated to a common bin and each target binding biomolecule is only allocated to one bin. Associating, in a circular or semi-circular bin chart on a display, identified bins with identified respective target binding biomolecule(s), wherein identified bins are illustrated as circle sectors in the bin chart. Based on the association between identified bins and identified respective target binding molecule(s) in the bin chart, selecting a subgroup of target binding biomolecules for further analysis by selecting one or more of the target binding biomolecule(s) of one or more of the bins.

The bin chart may be a circular or semi-circular chart and identified bins may be illustrated as circle sectors.

The competitive immunoassay may be performed on e.g. a Biacore instrument. The competitive immune assay format used may be a sandwich format, a tandem format or a premix format.

The target protein may be an antigen and the target binding biomolecules may be monoclonal antibodies binding to the same or different epitopes of the target. Alternatively, it may be a receptor-antibody system.

The processing unit may be any processor suitable for the task.

The binning unit may use a binning algorithm for allocating the target binding molecules in the different bins.

The display may be an electronic display, a paper etc.

A subgroup of target binding biomolecules may comprise one or more or all target binding molecules of one or more or all bins for further analysis.

The circular or semi-circular chart may be a pie chart, or a doughnut chart.

The bin chart may be a sunburst chart, which shows hierarchy through different series of rings: e.g. bin number, antibody name and e.g. antibody species.

A circle sector of a bin chart may be distinguished from neighbouring circle sectors in the bin chart by way of number, name, colour, pattern, border line type, border line colour, or coloured or patterned tag(s) at a perimeter of the circle sector.

A bin chart may comprise e.g. one colour for each circle sector/bin or circle sectors/bins not adjacent to each other in the chart may have the same colour/pattern. A circle sector/bin may be distinguished from adjacent bins by one, two or more deviating features such as colour and name.

The target binding biomolecules allocated to the same bin may block each other from binding to the target protein through a uni-directional blocking or bi-directional blocking or interact with the target protein through displacement.

The type of interaction between a target binding biomolecule allocated to a first bin and a target binding biomolecule allocated to a second bin may be a blocking interaction selected from a uni-directional blocking or bi-directional blocking, a non-blocking interaction or an interaction of undefined type.

The type of interaction between a target binding biomolecule allocated to a first bin and a target binding biomolecule allocated to a second bin may be displayed as arrows or lines between the first and second bin in the bin chart.

The direction of the arrow-head may indicate uni-direction binding. Dashed line may indicate uncertain binding.

The bin chart may be a doughnut chart and the arrows or lines may be arranged in the middle of the doughnut shape connecting separate bins with each other.

The target binding molecule may be a monoclonal antibody. The protein target may be a receptor. Such a receptor may be a cytokine receptor, a growth factor receptor, or an Fc receptor.

Bins with connections may be grouped together in the bin chart.

A connection between two bins visualize that the antibodies in those two bins have overlapping interaction pattern. Such bins are bin clusters.

Bins without connections to other bins may be arranged with a spacing to other bins in the bin chart. The spacing may be a small gap between adjacent circle sectors.

The display may be an electronic display and the display or underlying computing software may provide the ability of a user to modify the bin chart displayed by modifying one or more of colour, pattern, border line type, border line colour, tag pattern or colour at a perimeter of the bins.

Separate bins may be arranged in the bin chart based on number of target binding biomolecules in the bins.

According to a second aspect there is provided a system for qualifying a subgroup of target binding biomolecules from a larger group of target binding biomolecules for analysis. The system comprises: a competitive immunoassay with a target protein arranged to identify interactions between different pairs of target binding biomolecules, a processing unit arranged to generate interaction profiles from the identified interactions for said target binding biomolecules, a binning unit arranged to allocate each target binding biomolecules to a bin, wherein each bin represents an epitope family and target binding biomolecules sharing a common interaction profile are allocated to a common bin and each target binding biomolecule is only allocated to one bin, a display module arranged to, in a circular or semi-circular bin chart on a display, associate identified bins with identified respective target binding biomolecule(s), wherein identified bins are illustrated as circle sectors in the bin chart, a selection unit arranged to, based on the association between identified bins and identified respective target binding biomolecules(s), select a subgroup of target binding biomolecules for further analysis by selecting one or more of the target binding biomolecule(s) of one or more of the bins.

The selection unit may be a human being, or a programmed unit trained to choose subgroups of biomolecules from a larger set of biomolecules based on the information in a bin chart.

DETAILED DESCRIPTION

Figure 1:
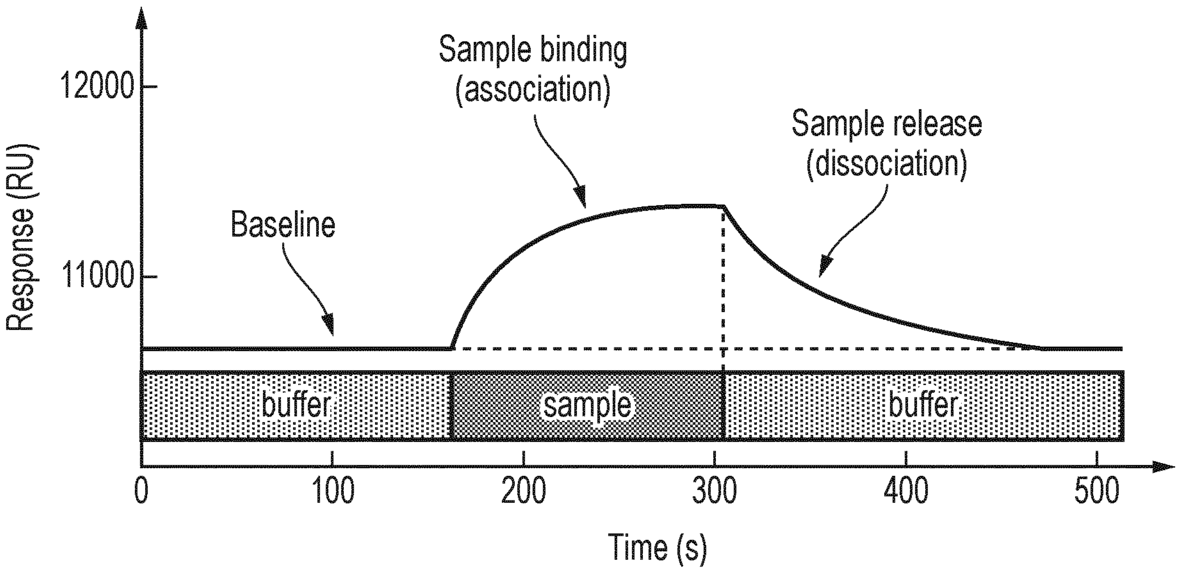
FIG. 1 shows a detection curve from the interaction between a sample and a target molecule using a Biacore instrument.

Analytical sensor systems arranged to monitor interactions between molecules, such as biomolecules, in real time may be based on label-free biosensors such as optical biosensors. A representative such biosensor system is the Biacore® instrumentation, which uses surface plasmon resonance (SPR) for detecting interactions between molecules in a sample and molecular structures immobilized on a sensing surface. The sample is passed over the sensor surface and the progress of binding directly reflects the rate at which the interaction occurs. A typical output from the Biacore® system and similar biosensor systems is a response graph or detection curve, see FIG. 1, describing the progress of the molecular interaction with time, including an association phase part and a dissociation phase part.

Detection curves produced by biosensor systems based on other detection principles, such as other optical methods and electrochemical methods will have a similar appearance.

Different high-throughput bioanalytical systems have been developed to enable efficient screening and characterization of bimolecular interactions. One example is the Biacore 8K instrument, wherein more than 1000 molecules may be screened in a day.

Such high-throughput systems may be valuable tools in epitope binning in early-stage screening of new therapeutics, vaccines, and in diagnostics. Epitope binning is a competitive immunoassay used to characterize and sort a library of for example monoclonal antibodies against a target protein. Antibodies against a similar target may be tested against all other antibodies in the library in a pairwise fashion to see if the antibodies block one another's binding to the epitope of the target protein, an antigen. Each antibody has a competitive blocking profile created against all of the other antibodies in the library. Epitope binning defines topological epitopes on an antigen in terms of the ability of the pairs of antibodies to bind simultaneously to the same antigen molecule. If two different antibodies can bind at the same time, they bind to topologically distinct epitopes. If they interfere with each other's binding, they bind to the same or overlapping epitopes. Closely related binning profiles indicate that the antibodies have the same or a closely related epitope and are "binned" together.

With epitope binning, top antibodies from each bin may be tested, allowing therapeutically relevant epitopes to be identified more quickly and cost efficiently. Thereby late stage failures and the number of antibody candidates may be increased without increases in costs or cycle time and thus, epitope binning increases overall probability of success.

Figure 2:
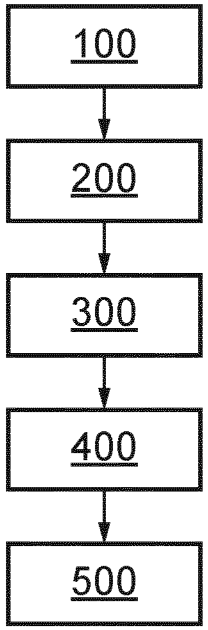
FIG. 2 illustrates the steps of a method for qualifying a subgroup of target binding molecules from a larger group of molecules for analysis.

A method of qualifying a subgroup of target binding biomolecules, such as antibodies, from a larger group of target binding molecules for analysis is illustrated in FIG. 2. In a first step 100 interactions between different pairs of target binding molecules are analysed against a target protein, an antigen, with a competitive immunoassay using a biosensor.

Figure 3A:
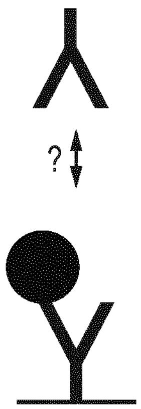
FIGS. 3*a*, 3*b* and 3*c* illustrate different binding assay formats which may be used in an epitope binning analysis.
Figure 3B:
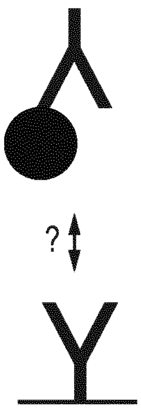
Figure 3C:
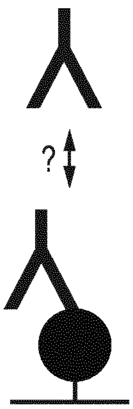

Different competitive immunoassay formats may be used when using e.g. a Biacore instrument as the Biacore 8K instrument: a sandwich format (see FIG. 3*a*), a tandem format (see FIG. 3*b*) or a premix assay format (see FIG. 3*c*) may be used. In the sandwich format a first antibody is either captured or immobilized on a sensor chip and an antigen molecule is injected and allowed to bind to the first antibody. Thereafter, a second antibody is injected and binds—or does not bind—to the antigen molecule depending on if it binds to the same (or overlapping) epitope as the first antibody. In the tandem format, an antigen molecule is immobilized on the sensor chip and a first antibody is injected and allowed to bind to the antigen molecule. A second antibody is then injected and binds—or does not bind—to an antigen molecule depending on if it binds to the same (or overlapping) epitope as the first antibody. In the premix format a first antibody is either captured or immobilized on the sensor chip. The antigen molecule is mixed with a second antibody, and then injected and binds to the first antibody—or does not bind—depending on if it binds to the same (or overlapping) epitope as the first antibody.

In a next step 200 of the method interaction profiles of the tested target binding biomolecules are generated from the identified interactions using a processing unit.

Thereafter, a step 300 is performed in which each target binding biomolecule is allocated to one or more bins. This may be performed using a binning unit, which may utilize a binning algorithm. A bin represents an epitope family, wherein target binding biomolecules sharing a common interaction profile are assigned to a common bin and each target binding biomolecule is only assigned to one bin. Identified bins with identified respective target binding biomolecule(s) may be associated 400 in a bin chart on a display (an electronic display or on paper). Based on the association between identified bins and identified respective target binding molecule(s) in the bin chart a subgroup of target binding biomolecules may be selected 500 for analysis by selecting one or more of the target binding biomolecule(s) of one or more of the bins.

In the evaluation, the response levels at each step in the binding analysis of either of the binding formats discussed above may be examined. This may help to compensate for variations in antibody concentration, and also to eliminate false negative answers, where lack of binding of the second antibody can be attributed to low binding or rapid dissociation between the first antibody and the antigen, rather than interference between a first and second epitope. Second antibodies that are classified as binding to independent epitopes may be ranked based on % dissociation after a specific time period using report points, or in some cases characterized in terms of the apparent dissociation rate constant from the antigen.

Figure 4:
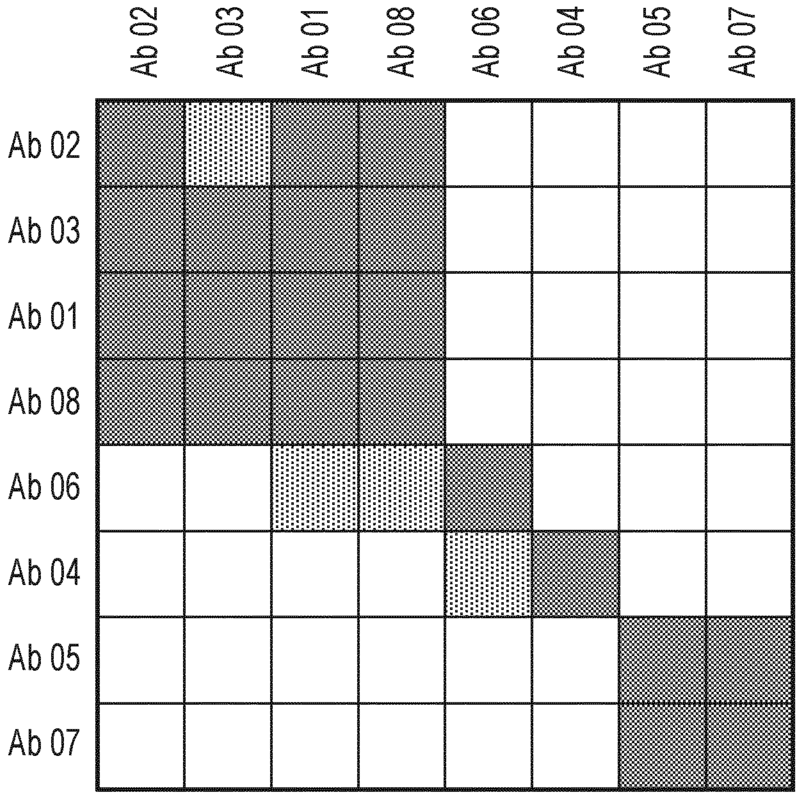
FIG. 4 shows a heat map from an epitope binning analysis.

Data from binning experiments may be displayed to a user in a so called heat map, see FIG. 4*a*, by using a binning algorithm. The heat map is a table where the binding response levels (or other parameters) are displayed for all analysed pairs of antibodies and different colours/patterns are used to distinguish antibodies that compete for the same epitope and those that do not. The heat map may comprise a grid of squares (coloured or patterned), which represent interactions between antibodies. Squares of a first colour/pattern represent a blocking interaction between two antibodies, and squares of a second colour/pattern represent that that they can simultaneously bind to the antigen in different locations. A third colour/pattern may be used to represent ambiguous interactions. Other colours/patterns may be used to represent "one-direction" interactions, in which blocking occurs when one antibody is attached to the antigen first. The heat map shown in FIG. 4 illustrates each tested interaction of a 8*8 binning experiment, where a dark gray cell illustrates "blocking", white cells mean "non-blocking" and light gray cells "uncertain" (borderline between blocking and non-blocking).

Heat maps as well as node charts, which are described and illustrated in US20150269312A1, may be difficult to quickly understand and to interpret the association of the experimental binning data therein, especially for inexperienced users. A simpler way of sorting and displaying data from binning experiments in a way such that also inexperienced users are able to quickly understand, interpret and extract information given from the binning experiments is needed.

Figure 5A:
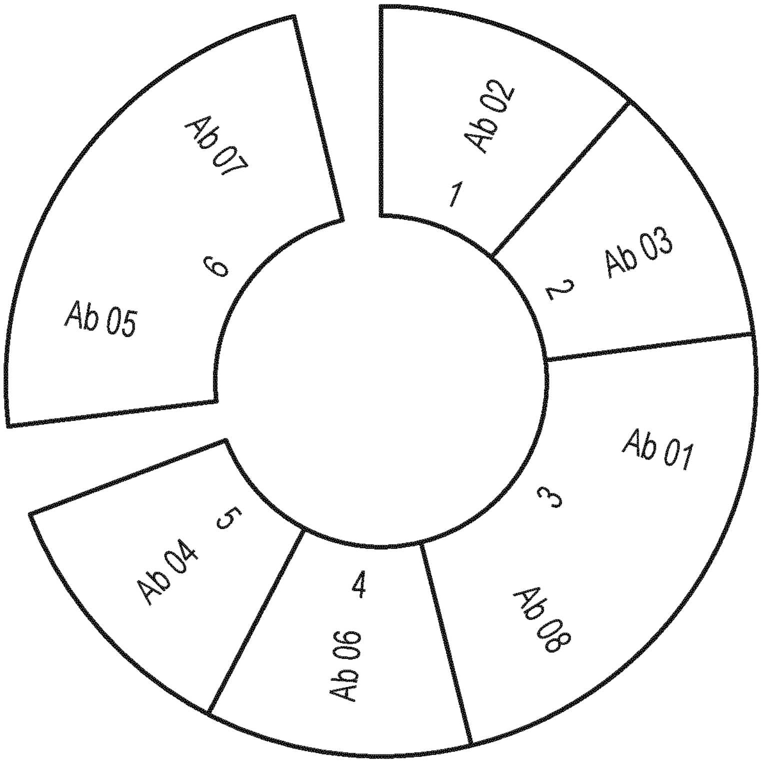
FIG. 5*a* shows a bin chart for an epitope binning analysis.

As illustrated in FIG. 5*a*, the data from a heat map (FIG. 4) identifying type of interaction between pairs of antibodies, is displayed in a bin chart. The bin chart may be a doughnut chart as shown in FIG. 5*a*. Alternatively, the bin chart may be a circular chart, a semi-circular chart, a sunburst chart, a bar chart or a line chart. The bin chart illustrates how the analysed antibodies (or other molecules such as receptors) shown in the heat map (FIG. 4) have been grouped according to their respective blocking/non-blocking behaviour. In the example shown, eight different antibodies have been grouped into six bins. Bin 3 contains the two antibodies Ab 01 and Ab 08, meaning that these two antibodies have the same pattern of blocking/non-blocking to all other antibodies tested in the epitope binning experiments. Antibodies with identical interaction pattern are grouped into the same bin. The antibodies in the other five bins deviate from that pattern in at least one interaction. In the bin chart shown in FIG. 5*a*, the antibodies are sorted in the same order as in the heat map shown in FIG. 4, starting at 12 o'clock and continuing clockwise. The different bins in the bin chart may be numbered from 1 and up, and/or they may be coloured or patterned in different colours/patterns.

Figure 5B:
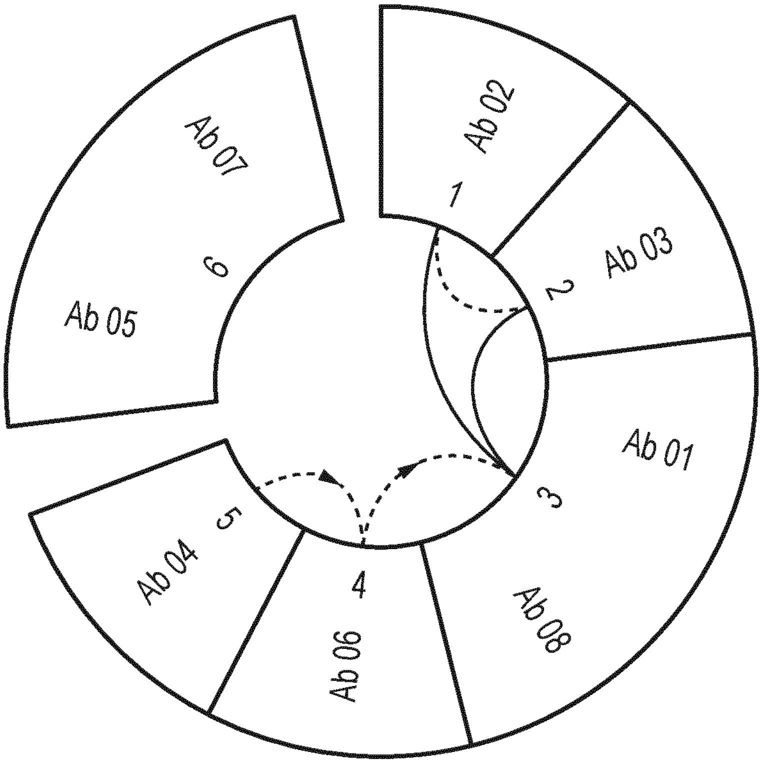
FIG. 5*b* shows the bin chart of FIG. 5*a* but with identified connections between bins.

The bin chart can include bin connections, i.e. identification of type of interaction between an antibody allocated to a first bin and an antibody allocated to a second bin, see FIG. 5*b*. A connection between two bins visualize that the antibodies in those two bins have overlapping interaction pattern. A bin with no connections to other bins means that none of the antibodies in that bin has an interaction with any of the antibodies in the other bins. Bin connections may be lines that connect two bins and contain information about the interaction type (blocking/non-blocking/uncertain) of the antibodies in these two bins. The interaction between bins may be illustrated as line/arrows connecting two bins. In the example shown in FIG. 5*b* the antibody in bin 1, Ab 02, has an overlapping interaction with the antibodies of bin 3, Ab 01 and Ab 08, and vice versa as is illustrated by the connecting line between the two bins. The dashed line between bin 1 and bin 2 illustrates that the interaction type is uncertain. The dashed line with an arrowhead seen between bin 5 and bin 4 illustrates that the interaction type is uncertain but the antibody in bin 4 may block the antibodies of bin 3 (uni-directional blocking). This is illustrated with the arrow head on the connection.

Figure 5C:
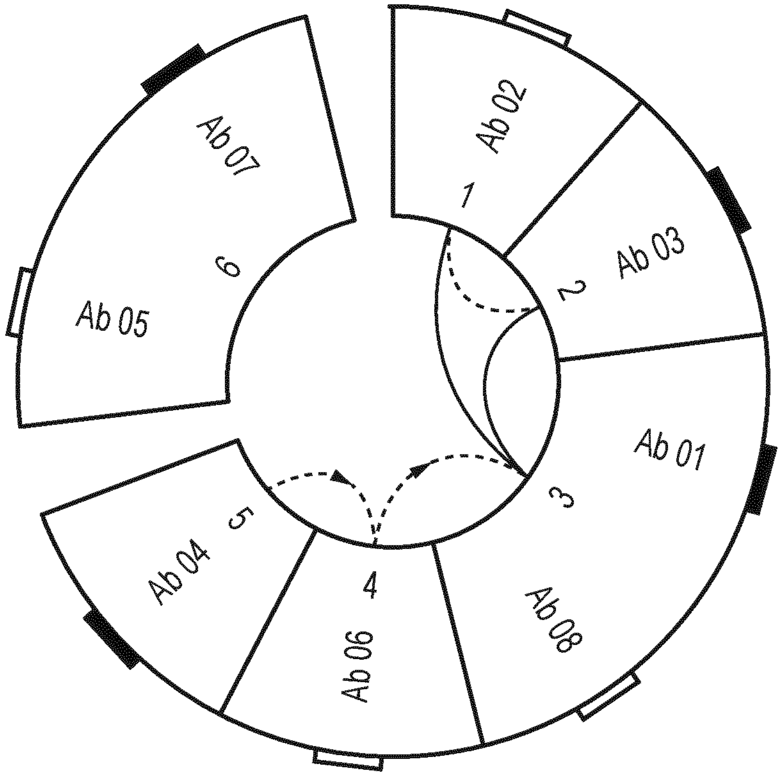
FIG. 5*c* shows a bin chart with tags for each antibody and a grouping of bins with a connection.

The bin chart could also be provided with tags for each antibody, see FIG. 5*c*. Such tags may e.g. be positioned on the bin chart perimeter of a doughnut (as illustrated), a circular, or a semi-circular bin chart, and they may be coloured/patterned to represent any type of data, for example antibody species. A legend explaining the colours/patterns can be shown. In a bin chart bins with connections may be grouped together and bins without connections to other bins may be illustrated with a spacing to other bins, see FIG. 5*c*. The bin chart of FIG. 5*c* is an exemplifying sunburst chart showing hierarchy through three series of rings: bin number, antibody name and e.g. antibody species.

Other sorting possibilities of the bins (not illustrated) than clockwise order of the antibodies in the heat map, may for example be by size (number of antibodies in the bin). The bins may have names instead of just numbers. A bin may be allowed to be selected in the bin chart upon when its immediate bin connections may be highlighted and the bins connected, and all non-connected bins dimmed out. For larger binning experiments this would simplify analysis of the bin connections. Instead of coloured/patterned tags on the bin chart perimeter antibody-related meta data values could be presented, for example their affinity, concentration etc. The meta data values could be presented on a coloured/patterned background that is automatically shaded from light to dark (colour/pattern gradient) to emphasize the magnitude of the meta data value.

Figure 6:
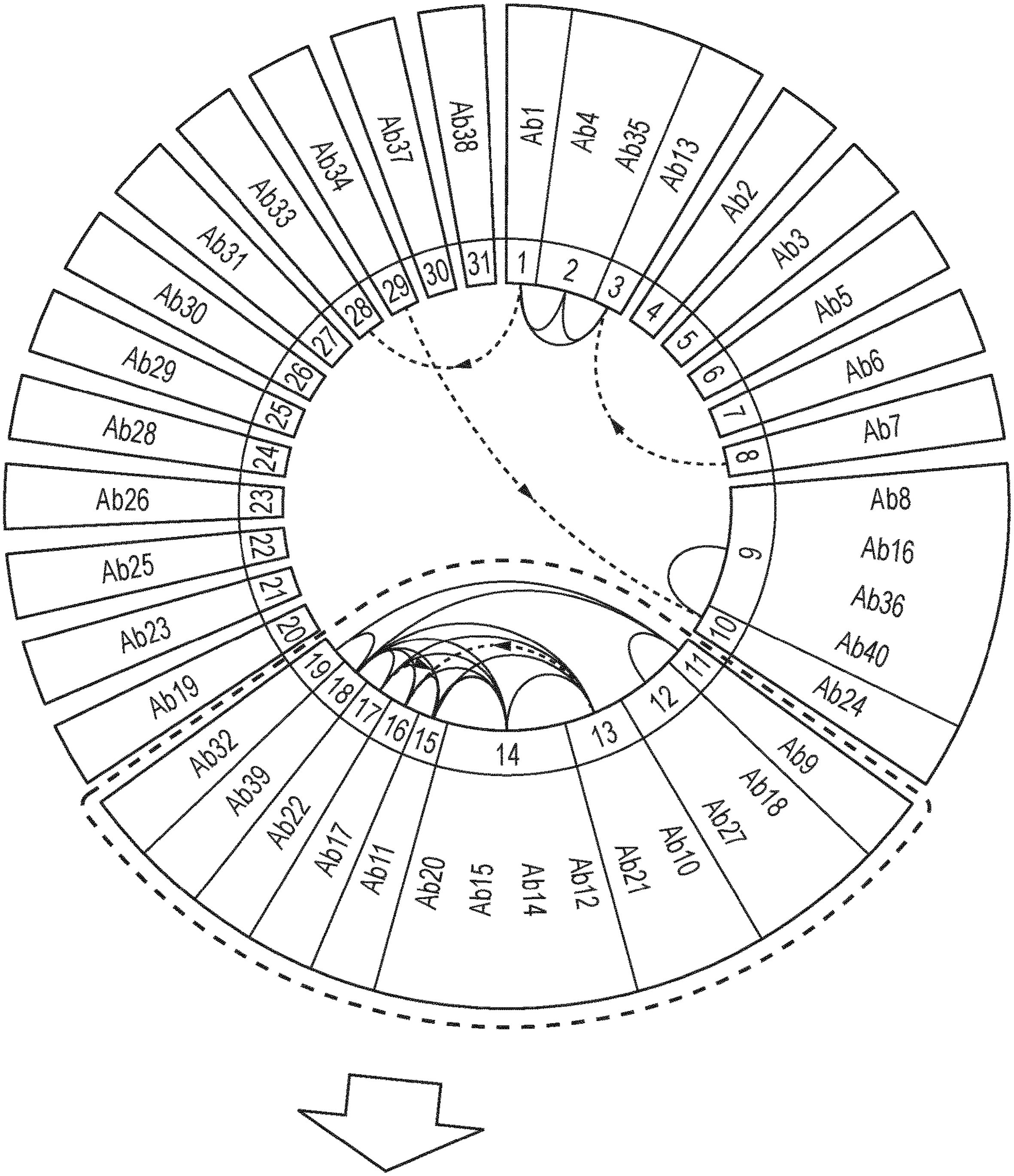
FIG. 6 shows an original bin chart with a plurality of bins and a second bin chart with a lower number of selected bins from the original bin chart, such that connections between specific bins becomes simpler to follow.
Figure 6:
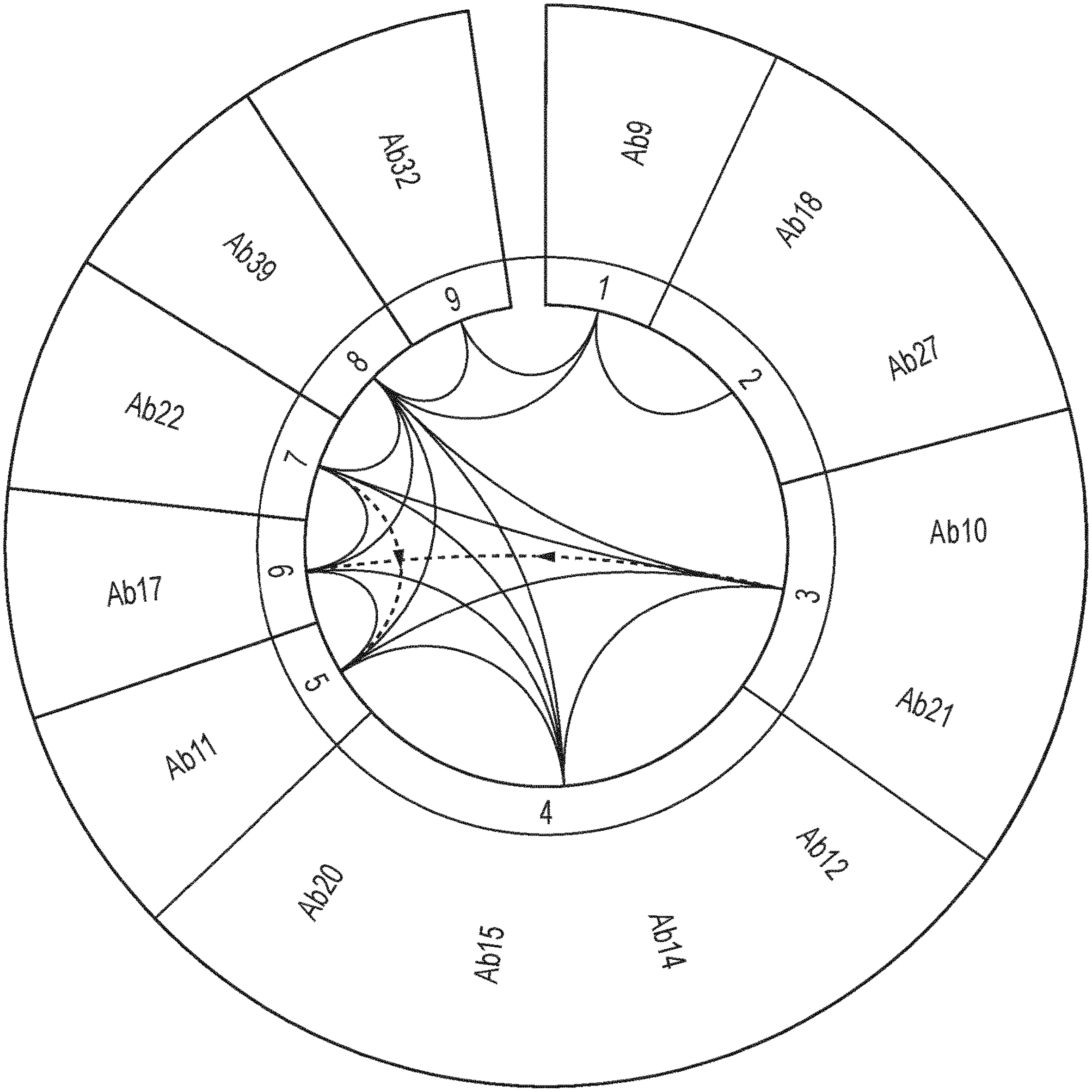

When analysing larger data sets, it could be possible to zoom in on different portions of a bin chart when displayed on a screen for a closer study of different bins and bin connections illustrated in the bin chart. In one embodiment the bins selected for closer inspection by a zoom in function may be represented in a new binchart only comprising the selected bins such that connections between specific bins becomes simpler to follow, e.g. as is schematically illustrated in FIG. 6.

As compared to the node chart of US20150269312A1, the connections illustrated in a bin chart (FIGS. 5*b*, 5*c*) are between bins. Such bin connections are easier to view and interpret since they are fewer than if presenting connections from each antibody.

It has been shown in user tests that interpretation of the basics of bin charts may be intuitively understood by most users, even inexperienced users The bin chart of circular, pie or sunburst shape may be seen as representing an antigen and the separate bins arranged in the chart as binding to different epitopes at the surface of the antigen.

Figure 7:
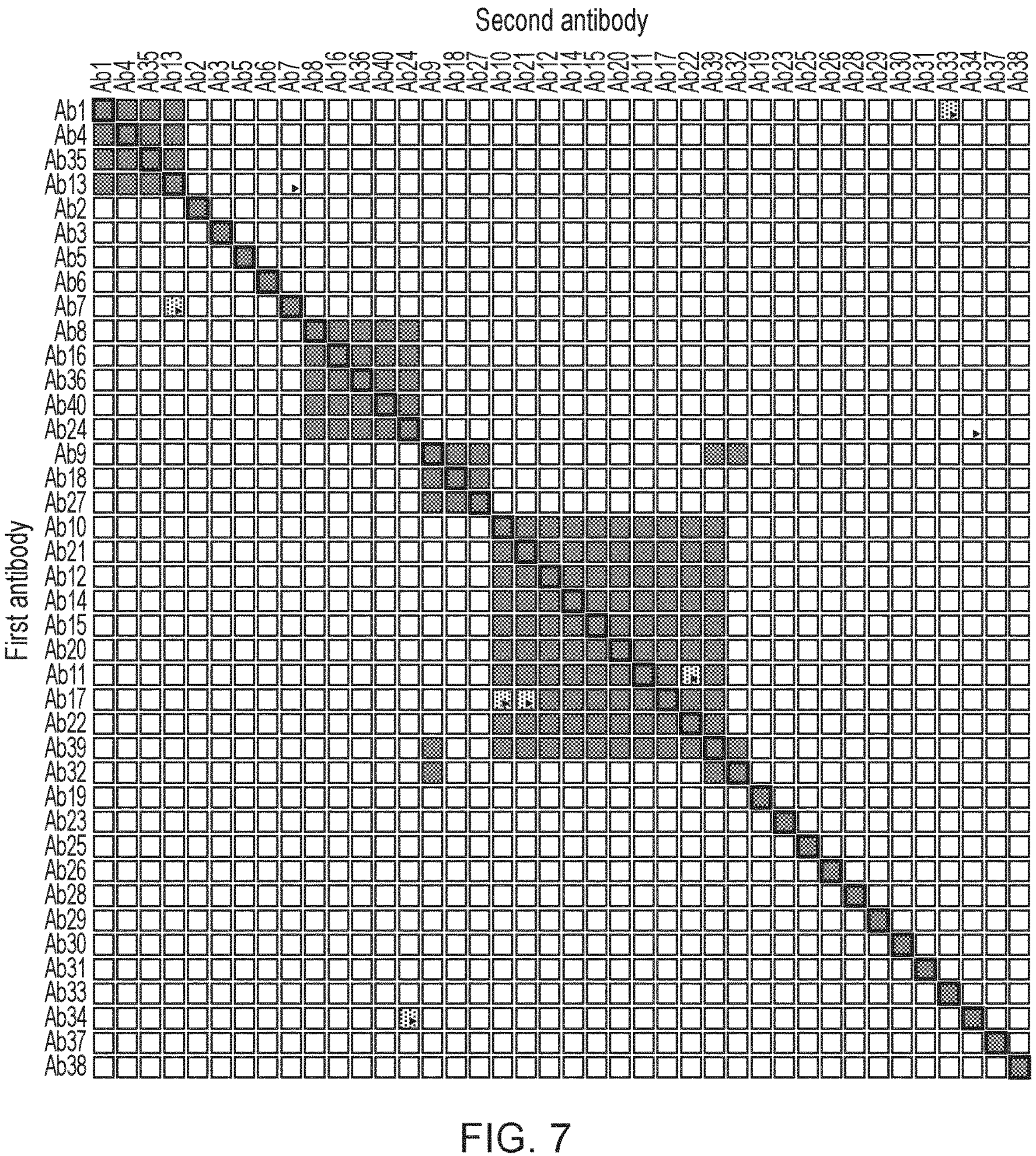
FIG. 7 shows a bin chart together with the corresponding heat map, wherein the antibodies are sorted in the same order in both the heat map and the bin chart. Here bin clusters are sorted after the lowest antibody number within each bin cluster.
Figure 7:
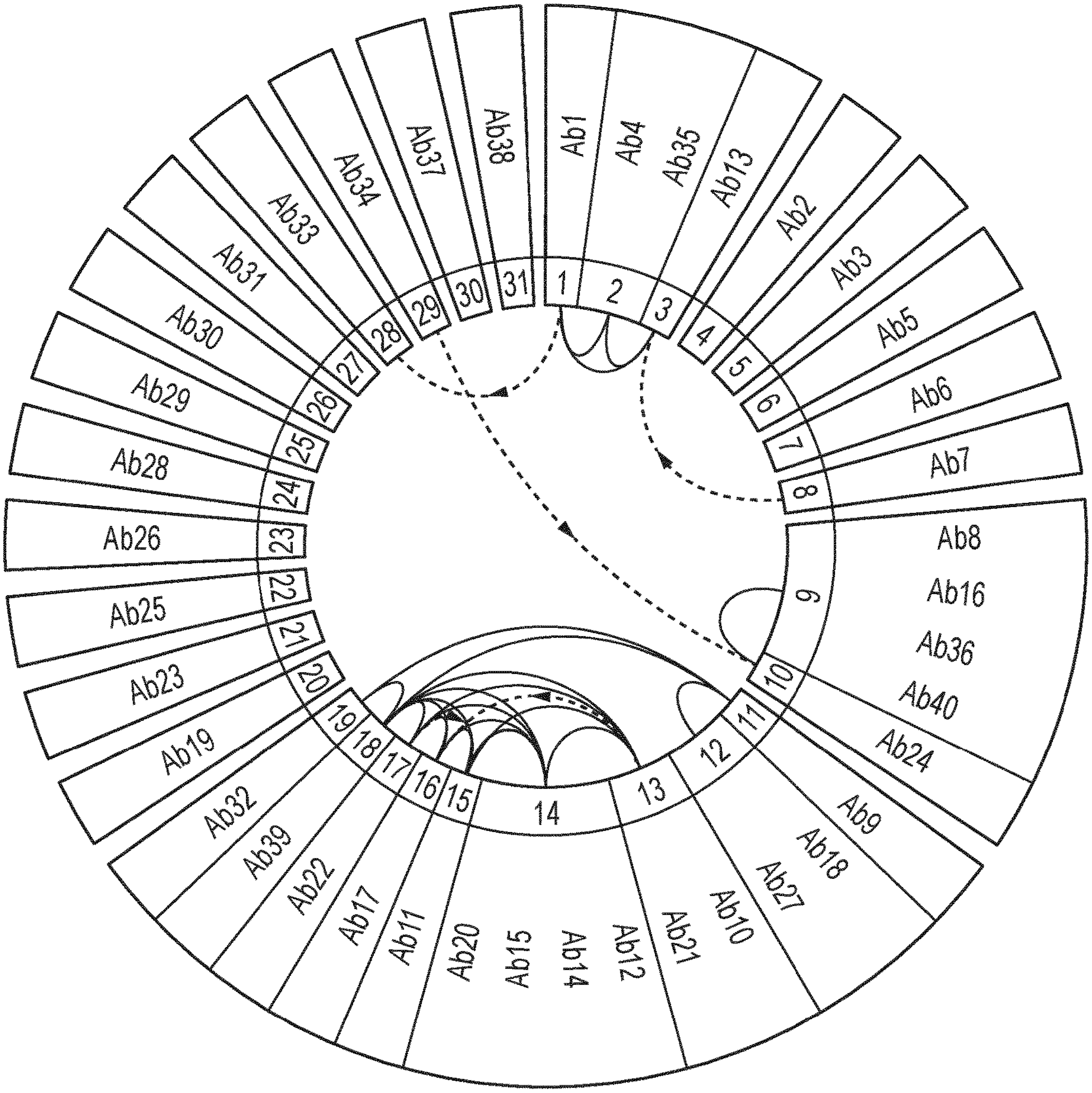

In one embodiment the bin chart is displayed together with the corresponding heat map, and as is mentioned the antibodies may be sorted in the same order in both the heat map and in the bin chart. The binning algorithm may be arranged to sort the bin clusters based on order of appearance in the experimental tests. In FIG. 7 this is illustrated by sorting the bin clusters after the lowest antibody number within each bin cluster. The binning algorithm may also be arranged to sort the bin clusters differently, for example by order of size of the bin clusters. With bin cluster is here meant bins that are grouped together as the antibodies in those bins have overlapping interaction pattern.

The binning algorithm identifies antibodies that block simultaneous binding to the antigen in an, to each other, identical manner. Such identification may, for example, use machine learning techniques that can be learned following training where blocking/non-blocking determinations for each antibody pair is done by a user (setting cut-offs). The antibodies are defined as bins and may be displayed as bins in a bin chart.

In various embodiments, the blocking/non-blocking determination for each antibody pair may be undertaken by a user (setting cut-offs) with software then helping to sort the antibodies in groups that block each other, and to determine if the groups contain antibodies with identical blocking partners.

For example, groups (bins) of antibodies may be presented as segments in a bin chart. A user (or trained algorithm) may then change which antibody pairs are classed for blocking and then the sorting and grouping will accordingly be automatically changed.

For example, for antibodies A, B, C and D: if A blocks B and C whiles B block A and C while C blocks A and B then A, B, C can define a bin; but if B also blocks D while A and C do not block D then A and C are provided in a separate bin from B; then in a graphic representation chart the lines in a bin chart can shows if the antibodies in two bins block each other so, in this case, the A, C bin will have a line to B bin and the B bin will have a line to the D bin. Bins with lines between are then kept together in the graphic representation chart while bins with no blocking with other bins are separated by segments. Such a graphic representation chart (not shown), or data representative thereof, may thus provide a clear dynamic automatically-updating visualisation, or representation, of the relationships between various antibody pairs that thereby enable faster user (or machine) interpretation thereof, and thus an improved throughput for system for qualifying a subgroup of target binding biomolecules from a larger group of target binding biomolecules. Such a technique may also be used to provide input data, for example, for automated robotically-controlled processing equipment used for screening for candidate subgroups of target binding biomolecules.

Although the description above contains a plurality of specificities, these should not be construed as limiting the scope of the concept described herein but as merely providing illustrations of some exemplifying embodiments of the described concept. It will be appreciated that the scope of the presently described concept fully encompasses other embodiments which may become obvious to those skilled din the art, and that the scope of the presently described concept accordingly is not to be limited. Reference to an element in the singular is not intended to mean "one and only one" unless explicitly so stated, but rather "one or more". All structural and functional equivalents to the elements of the above-described embodiments that are known to those of ordinary skill in the art are expressly incorporated herein and are intended to be encompassed hereby.

The invention claimed is:

1. A method of qualifying a subgroup of target binding biomolecules from a larger group of target binding biomolecules for analysis, the method comprising:

in a competitive immunoassay including a target protein, identifying interactions between different pairs of the target binding biomolecules, using a processing unit, generating interaction profiles for said target binding biomolecules from said identified interactions, using a binning unit, allocating each target binding biomolecule to a bin, wherein each bin represents an epitope family and target binding biomolecules sharing a common interaction profile are allocated to a common bin and each target binding biomolecule is only allocated to one bin, associating, in a circular or semi-circular bin chart on a display, identified bins with identified respective target binding biomolecule(s), wherein identified bins are illustrated as circle sectors in the bin chart, and wherein the bin chart includes bin connections identifying a type of interaction between antibodies allocated in respective bins, and based on the association between identified bins and identified respective target binding molecule(s) in the bin chart, selecting a subgroup of target binding biomolecules for further analysis by selecting one or more of the target binding biomolecule(s) of one or more of the bins.

2. The method of claim 1, wherein the circular or semi-circular chart is a pie chart, or a doughnut chart.

3. The method of claim 1, wherein a circle sector of a bin chart is distinguished from neighbouring circle sectors in the bin chart by way of number, name, colour, pattern, border line type, border line colour, or coloured or patterned tag(s) at a perimeter of the circle sector.

4. The method of claim 1, wherein target binding biomolecules allocated to the same bin block each other from binding to the target protein through a uni-directional blocking or bi-directional blocking or interact with the target protein through displacement.

5. The method of claim 1, wherein a type of interaction between a target binding biomolecule allocated to a first bin and a target binding biomolecule allocated to a second bin is a blocking interaction selected from a uni-directional blocking or bi-directional blocking, a non-blocking interaction or an interaction of undefined type.

6. The method of claim 5, wherein the type of interaction between a target binding biomolecule allocated to a first bin and a target binding biomolelule allocated to a second bin is displayed as arrows or lines between the first and second bin in the bin chart.

7. The method of claim 6, wherein the bin chart is a doughnut chart and said arrows or lines are arranged in the middle of the doughnut shape connecting separate bins with each other.

8. The method of claim 1, wherein the target binding molecule is a monoclonal antibody.

9. The method of claim 1, wherein the protein target is a receptor.

10. The method of claim 1, wherein bins with connections are grouped together in the bin chart.

11. The method of claim 1, wherein bins without connections to other bins are arranged with a spacing to other bins in the bin chart.

12. The method of claim 1, wherein the display is an electronic display and the display or underlying computing software provides the ability of a user to modify the bin chart displayed by modifying one or more of colour, pattern, border line type, border line colour, tag pattern or colour at a perimeter of the bins.

13. The method of claim 1, wherein separate bins are arranged in the bin chart based on number of target binding biomolecules in the bins.

14. A system for qualifying a subgroup of target binding biomolecules from a larger group of target binding biomolecules for analysis, the system comprising:

a competitive immunoassay with a target protein arranged to identify) interactions between different pairs of target binding biomolecules, a processing unit arranged to generate interaction profiles from the identified interactions for said target binding biomolecules, a binning unit arranged to allocate each target binding biomolecules to a bin, wherein each bin represents an epitope family and target binding biomolecules sharing a common interaction profile are allocated to a common bin and each target binding biomolecule is only allocated to one bin, a display module arranged to, in a circular or semi-circular bin chart on a display, associate identified bins with identified respective target binding biomolecule (s), wherein identified bins are denoted as circle sectors in the bin chart, and wherein the bin chart includes bin connections identifying a type of interaction between antibodies allocated in respective bins, and a selection unit arranged to, based on the association between identified bins and identified respective target binding biomolecules(s), select a subgroup of target binding biomolecules for further analysis by selecting one or more of the target binding biomolecule(s) of one or more of the bins.

* * * * *